United States Patent [19]
Policello

[11] Patent Number: 5,998,331
[45] Date of Patent: Dec. 7, 1999

[54] ORGANOAMINE SILOXANE ALKOXYLATE SURFACTANTS

[75] Inventor: George A. Policello, Ossining, N.Y.

[73] Assignee: Witco Corporation, Greenwich, Conn.

[21] Appl. No.: 08/812,844

[22] Filed: Mar. 6, 1997

Related U.S. Application Data

[60] Provisional application No. 60/012,936, Mar. 6, 1996, and provisional application No. 60/015,259, Apr. 10, 1996.

[51] Int. Cl.⁶ .......................... A01N 25/24; A01N 39/02; B01F 17/42; B01F 17/54
[52] U.S. Cl. ...................... 504/116; 71/DIG. 1; 424/407; 504/206; 510/421; 510/466; 516/55; 516/77; 516/204
[58] Field of Search .................................. 252/351, 357; 424/407; 504/323, 116; 71/DIG. 1; 510/421, 466; 516/55, 77, 198, 204

[56] References Cited

U.S. PATENT DOCUMENTS

| | | | |
|---|---|---|---|
| 3,389,160 | 6/1968 | Reid | 252/351 X |
| 4,973,352 | 11/1990 | Heinrich et al. | 71/DIG. 1 |
| 5,104,647 | 4/1992 | Policello | 424/407 X |
| 5,360,571 | 11/1994 | Kilgour et al. | 510/466 X |
| 5,504,054 | 4/1996 | Murphy | 71/DIG. 1 |
| 5,658,851 | 8/1997 | Murphy et al. | 71/DIG. 1 |

FOREIGN PATENT DOCUMENTS

| | | |
|---|---|---|
| 535 596 | 7/1993 | European Pat. Off. . |
| 43 18 537 | 12/1994 | Germany . |

OTHER PUBLICATIONS

Sandbrink et al., *Pest Sci*.38: 272–273 (1993).
Gaskin et al., *Pest Sci*.38: 185–192, (1993).
Snow, *Langmuir* 9: 424–430 (1993).
Moriarty et al., *Synthetic Communications*, 15(7): 649–655 (1985).

*Primary Examiner*—Richard D. Lovering
*Attorney, Agent, or Firm*—Edward K. Welch, II; Andrew S. Reiskind; Timothy X. Witkowski

[57] ABSTRACT

It has been discovered that organoamine modified siloxane alkoxylates overcome the antagonism associated with non-ionic trisiloxane alkoxylates on pesticide uptake in plants. The organoamine modified siloxane alkoxylates of the present invention have the average general formula: $AMe_2SiO[(Me)_2SiO]_x[MeSi(Z)O]_ySiMe_2A$, wherein $x=0$ to 1, $y=0$ to 2, with the proviso than when $y=0$, A is Z, A= is Z or Me, $Z=RO(R^1)_n, R^2N(R^3)_2$, R is a divalent organic group having from 2 to 4 carbon atoms, $R^1$ is an alkyleneoxide group containing 2 to 4 carbon atoms, $R^2$ is a divalent organic group containing 2 to 6 carbons, $R^3$ may be hydrogen, an alkyl radical with 1 to 4 carbons, an amino alkyl of one to four carbons, or an alkyl of 2 to 4 carbon atoms which may have hydroxy substitutions thereon. Each $R^3$ may be the same or different.

When $R^1$ is oxyethylene, n is from 1 to 10, preferably 2 to 5. When $R^1$ is oxypropylene, n is from 1 to 5, preferably from 2 to 4. When $R^1$ is a mixture of oxyethylene and oxypropylene n is from 2 to 10, preferably from 2 to 6, providing that the molar ratio of oxyethylene to oxypropylene is from 0.11 to 9. When $R^1$ is butylene oxide, there must also be sufficient ethylene oxide such that the siloxane is water dispersible or soluble.

22 Claims, No Drawings

ORGANOAMINE SILOXANE ALKOXYLATE SURFACTANTS

This application claims priority from U.S. Provisional Application No. 60/012,936, filed Mar. 6, 1996, and U.S. Provisional Application No. 60/015,259, filed Apr. 10, 1996.

BACKGROUND OF THE INVENTION

Many pesticides require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, or to provide penetration of the herbicide into the plant cuticle. These adjuvants are either provided as a component in an adjuvant formulation or used as an additive in herbicide formulations.

Gaskin, et al., (*Pestic. Sci.* 1993, 38, 185–192) demonstrated that some trisiloxane ethoxylates (TSE), such as Silwet L-77® surfactant (available from OSi Specialties, Inc. of Danbury, Conn.), can antagonize cuticular penetration of glyphosate herbicide into grasses, when compared to the herbicide alone. The term antagonism is used to indicate that the treatment of herbicide plus adjuvant is less effective than the comparative herbicide treatment.

This antagonism can be mitigated if the number of ethylene oxide (EO) units contained in the TSE is increased to 17 or more; however, superspreading of the TSE is dramatically reduced once the degree of ethoxylation exceeds about 12 EO and TSE's containing the higher EO adducts show spreading properties similar to conventional nonsilicone surfactants.

Sandbrink, et al., (Pest. Sci. 1993, 38, 272–273) published that a TSE antagonized glyphosate performance relative to glyphosate alone in the control of *Panicum maximum* Jacq.

Snow, S. A. et. al., *Langmuir*, 1993, 9, 424–30, discusses the physical properties and synthesis of novel cationic siloxane surfactants. These siloxanes are based on the reaction of a chloropropyl modified trisiloxane with an alkanolamine, such as N-methylethanolamine, which was further reacted with a halide to make a quaternary surfactant.

Petroff, et al., (EP 92116658) describes the use of cationic, quaternary trisiloxanes to enhance the efficacy of glyphosate on velvetleaf, a broadleaf weed. Henning, et al., (DE4318537) describes cationic siloxanyl modified polyhydroxy hydrocarbon or carbohydrate for use with plant protection agents. These compounds are derived from a saccharide containing 1 to 10 pentose and/or hexose units, modified with a quaternary ammonium group, and a siloxane moiety.

SUMMARY OF THE INVENTION

The present invention teaches the composition of organoamine modified siloxane alkoxylates and their use as adjuvants, for pesticides containing an acid functional group or an acid derivative, for example the corresponding esters or salts, heretofore known as acid functional pesticides. These unique siloxanes provide superspreading, as defined below, on difficult to wet surfaces, such as waxy plants, and enhance the uptake of agrichemicals into plants as compared to conventional TSE's. Optionally, the organoamine modified siloxane alkoxylates of this invention may be blended with conventional trisiloxane alkoxylates.

The composition of the present invention is useful as a tank side additive, or as a component in a herbicide formulation. In addition the compositions of the present invention are useful as adjuvants for other pesticides, such as, fungicides, insecticides, plant growth regulators, acaracides and the like.

DETAILED DESCRIPTION OF THE INVENTION

The present invention provides novel organoamine modified siloxane alkoxylates that are useful as adjuvants for acid functional pesticides. These compositions are especially useful in overcoming the antagonistic effects on pesticide uptake associated with superspreading, trisiloxane alkoxylates. The compositions of the present invention provide enhanced spray coverage relative to conventional wetting agents. In addition, these products provide a low aqueous surface tension (<23 mN/m at 0.1 wt %), which is necessary and desirable for superspreading of pesticide solutions.

COMPOSITION

The organoamine modified siloxane alkoxylates of the present invention have the average general formula: $AMe_2SiO[(Me)_2SiO]_x[(Me)Si(Z)O]_ySiMe_2A$, wherein x=0 to 1, preferably 0, y=0 to 2, preferably 1, with the proviso that when y=0, A is Z. A is selected from the group of Me or Z, preferably, Me. $Z=RO(R^1)_nR^2N(R^3)_2$, wherein R is a divalent organic group having from 2 to 4 carbon atoms, $R^1$ represents an alkyleneoxide group containing 2 to 4 carbon atoms, $R^2$ is a divalent organic group containing 2 to 6 carbons, preferably 2 to 4 carbons, each optionally OH substituted, $R^3$ may be hydrogen, an alkyl radical with 1 to 4 carbons, an amino alkyl of one to four carbons, or an alkyl of 2 to 4 carbon atoms which may have hydroxy substitutions thereon. Each $R^3$ may be the same or different.

The Z groups may include protonated amines, i.e., where there is a hydrogen ion attached to the nitrogen in the Z group, which can occur in the organoamine modified siloxanes under acidic conditions. Though not included in the formula above, also contemplated herein are quaternary versions of Z, i.e., where there is a third $R^3$ group on the nitrogen in Z, but said quaternary compounds are not preferred for use in the present invention.

When $R^1$ is oxyethylene, n is from 1 to 10, preferably 2 to 5. When $R^1$ is oxypropylene, n is from 1 to 5, preferably from 2 to 4. When $R^1$ is a mixture of oxyethylene and oxypropylene, n is from 2 to 10, preferably from 2 to 6, providing that the molar ratio of oxyethylene to oxypropylene is from 0.11 to 9. When $R^1$ is butylene oxide, there must also be sufficient ethylene oxide such that the siloxane is water dispersible or soluble. Additionally, when $R^1$ is a mixture of oxyalkylenes, it may be blocked or random. One skilled in the art will understand the advantages in the position of the oxyethylene relative to the oxypropylene, when the alkyleneoxide group is blocked.

Preferred Z structures are wherein R is propylene, $R^1$ is oxyethylene, $R^2$ is ethylene or propylene, n=2 to 4 and $R^3$ is 2-hydroxyethyl, 2-hydroxypropyl, 3-hydroxypropyl, propyl, or ethyl. Preferred cationic siloxanes are trisiloxanes.

In addition the compositions of the present invention optionally may include nonionic siloxane alkoxylates of the general formula:
$R^5Me_2SiO[Me_2SiO]_f[MeSi(Q)O]_gSiMe_2R^5$ wherein f=0 to 1, preferably 0, g=1 to 2, preferably 1, $Q=C_dH_{2d}O(C_2H_4O)_t(C_3H_6O)_wR^4$, d=2 to 4, preferably 3, t=3 to 12, preferably 4 to 8, w=0 to 8, providing that when w is>0, (t+w) is preferably between 5 and 12. $R^4$ is hydrogen, acetyl or a hydrocarbon radical between 1 and 4 carbon atoms. $R^5$ is Q, an alkyl of one to four carbons or a hydroxyl group. The preferred nonionic siloxane alkoxylates are trisiloxane alkoxylates, which have f=0, g=1, d=3, t=4 to 8, w=0, $R^4$ is H or Me.

The compositions of the present invention can also optionally contain any of certain nonionic surfactants which do not detract from the efficacy of the composition. Examples include alkyl alkoxylates corresponding to the formula $R^A$—O$(R^c)_cR^E$ wherein $R^A$ and $R^E$ each denote hydrogen or $C_1$ to $C_{12}$ alkyl (straight or branched chain), $R^c$ denotes alkoxy groups containing 2 or 3 carbon atoms each, and the subscript c is selected so that the molecular weight of the surfactant is 500 to 15,000 and preferably 1,000 to 8,000. Preferably, one of $R^A$ and $R^E$ is alkyl. Preferred embodiments include compounds containing 0 to 300 ethoxy units and 1 to 300 propoxy units. More preferably, the ethoxy content of the compound is 10 to 90 weight percent and more preferably 10 to 50 weight percent of the compound.

Other examples of useful nonionic surfactants include alkoxylated diamines of the formula $(H(R^T)_T)_2NC_2H_4N((R^T)_TH)_2$ wherein $R^T$ denotes alkoxy groups containing 2 or 3 carbon atoms each, and the subscript T is selected so that the molecular weight of the alkoxylated diamine is 1,000 to 15,000. Preferably, ethoxy units comprise 10 to 90% and more preferably 20 to 50% of the polyalkoxylate chains. Other examples of useful nonionic surfactants are glycosides.

The compositions of the present invention also optionally include ingredients for use herein which are pesticides, especially acid functional ones, e.g., compounds that contain at least one carboxylic, sulfonic or phosphonic acid group which is in the form of the free acid or a salt or ester thereof. The term pesticide means any compound used to destroy pests, e.g., insecticides, rodenticides, fungicides, and herbicides, and is also used herein to include plant growth regulatory compounds. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, cyclohexanediones, aryloxyphenoxypropanoates, dichlobenil, isoxaben, and bipyridylium compounds.

MANUFACTURE

The organoamine modified siloxanes of the present invention may be made by the hydrosilation of a hydridosiloxane (which are commercially available and may be made as known in the art) and an allyl started polyalkyleneoxide, which is also available commercially.

Epoxy terminated, allyl polyethyleneoxide can be prepared by the method outlined by Xue-Ping Gu, et al, (Synthesis of Glycol Diglycidyl Ethers Using Phase-Transfer Catalysis; in *Synthesis Communications June/July* 1985, p. 649–651) from an epoxide and commercially available allyl started polyalkylene oxides. Said material is then hydrosilated onto the siloxane and the epoxy is reacted with an amine. Alternatively a hydroxy terminated (i.e., uncapped) allyl started polyalkyleneoxide may be hydrosilated onto the siloxane and then reacted with an aziridine. Said reactions are known in the art.

The nonionic siloxane and pesticides are commercially available and their manufacture is known in the art.

USE

The organoamine modified siloxanes primarily are intended for use in the agricultural field as adjuvants for pesticide, especially acid functional pesticides, containing aqueous end-use formulations. The siloxanes are added directly to a spray tank along with an acid functional pesticide, or as part of a pesticide formulation. They are used in effective amount, that is, an amount which is sufficient to cause the pesticide to function effectively in the formulation. When used as a tankside additive, the organoamine modified siloxanes are present at weight concentrations between 0.01% and 5.0%, preferably between 0.025% and 0.5%, but in "in can" formulations, the organoamine modified siloxanes may be present at concentrations that will deliver between 0.01% and 5.0% to the final use dilution, preferably between 0.025% and 0.5%, of the final use dilution.

When the compositions of the present invention are used in conjunction with a nonionic siloxane alkoxylate, the weight ratio of the nonionic siloxane alkoxylate to the organoamine modified siloxane alkoxylate is between 5:95 and 60:40. When the compositions of the present invention contain a nonionic component which is an alkyl alkoxylate or alkoxylated diamines, as described hereinabove, the weight ratio of such nonionic component to the organoamine modified siloxane alkoxylate should be between 5:95 and 90:10. Blends of multiple components may be accomplished by physically mixing the components together as a formulation, or by adding them separately to a spray mixture at point of use.

The organoamine modified siloxanes of the present invention may also be used generally as surface active agents in aqueous formulation where there is an acid functionalized component, including, but not limited to, surfactants, wetting agents and softeners for textiles, as flowing and leveling agents in coatings, in hair care products and creams for personal care applications and as anti-static agents and softeners for laundry products. Other uses for the present composition will be obvious to those of skill in the art.

EXAMPLES

The following examples are presented to further illustrate and explain the present invention and should not be taken as limiting in any regard. Unless otherwise indicated, all parts and percentages are by weight, and are based on the weight at the particular stage of the processing being described.

Example 1 a. Organoamine Modified Trisiloxane Alkoxylates:

12.0 g (0.055 moles) of epoxy terminated, allyl polyethyleneoxide (2 EO, 15.2% $C_2O$) and 98.4 g (0.442 moles) of heptamethyltrisiloxane were combined in a 250 mL, 4 neck round bottom flask, equipped with a mechanical agitator, a Claisen adapter containing a reflux condenser and a thermometer (with Therm—o—Watch), a nitrogen bypass, and a 100 mL addition funnel. The mixture was heated to 85° C. and catalyzed with 0.05 mL of chloroplatinic acid solution (1% in ethanol). The reaction mixture exothermed to 102° C.

after one minute. The remaining 114.6 g (0.523 moles, corresponding to a total excess of 31%) of epoxy terminated, allyl polyethyleneoxide was added from the addition funnel at a rate sufficient to maintain the reaction temperature at approximately 100° C. Once all of the of epoxy terminated, allyl polyethyleneoxide was added, the hydrosilation product was stirred for 2 hours at 100° C. The reaction mixture showed no traces of SiH when introduced to a fermentation tube containing KOH/water/ethanol solution. The product was then filtered through a fine filter pad and stripped on a Rotovap for 1.5 hours at 70° C. and to 1.0 mm Hg to afford a clear amber liquid with an epoxy content of 8.6 wt % (100% of expected epoxy).

The epoxy modified trisiloxane intermediate (50.0 g; 0.107 moles), along with 21.1 g (0.2 moles) of diethanolamine (corresponding to an 1.88 mole % molar excess), and 30.5 g of 2-propanol (solvent), were added to a 250 mL, 4 neck round bottom flask, equipped with a mechanical agitator, a Claisen adapter containing a reflux condenser and a thermometer (with Therm—o—Watch), and a nitrogen bypass. The mixture was heated to 80° C., and catalyzed with 0.13 g titanium (IV) butoxide. The reaction time was approximately 8 hours, at which time the temperature was adjusted to 70° C., and 1.0 g water was added to deactivate the catalyst. The mixing time was approximately 1 hour. The product was then filtered through a fine filter pad and stripped on a Rotovap for 1.5 hours at 70° C. and to 1.0 mm Hg to afford a clear amber liquid with a Brookfield viscosity of 280 cps at 25° C. (spindle LV-3, 60 rpm).

The structures for the epoxy terminated, allyl polyethyleneoxide, and the organoamine modified trisiloxane alkoxylate, were confirmed by $^{29}$Si and $^{13}$C NMR. The organoamine modified trisitoxane alkoxylate used here as an example, is shown as CATSIL-1, in Table 1. Other compositions of cationic modified trisiloxanes (x=0, y=1) shown below were prepared according to this procedure.

Tables 1 and 2 describes the organoamine modified trisiloxane alkoxylates used herein as illustrative examples of the compositions of the present invention.

TABLE 1

| Reference | Nominal Formula of the Z Group |
| --- | --- |
| CATSIL 1 | $C_3H_6O(C_2H_4O)_2CH_2CH(OH)CH_2N[CH_2CH_2OH]_2$ |
| CATSIL 2 | $C_3H_6O(C_2H_4O)_4CH_2CH(OH)CH_2N[CH_2CH_2OH]_2$ |
| CATSIL 3 | $C_3H_6O(C_2H_4O)_8CH_2CH(OH)CH_2N[CH_2CH_2OH]_2$ | b. Comparative Silicone Based Surfactants:

Table 2 provides structural information on two comparative trisiloxane alkoxylates that are commercially used as wetting agents for agrichemicals and two experimental trisiloxane alkoxylates with higher ethyleneoxide content. These materials were prepared by standard hydrosilation of an allyl terminated polyether with an heptamethyl trisiloxane Si-H intermediate. The SiH intermediates were prepared by acid equilibration as is known in the art.

TABLE 2

Description of Conventional Trisiloxane Alkoxylates

| Reference | $Me_3SiO[MeSi(Q)O]_1SiMe_3$ Q Group |
| --- | --- |
| Sil-A | $C_3H_6O(C_2H_4O)_8CH_3$ |
| Sil-B | $C_3H_6O(C_2H_4O)_8H$ |

TABLE 2-continued

Description of Conventional Trisiloxane Alkoxylates

| Reference | $Me_3SiO[MeSi(Q)O]_1SiMe_3$ Q Group |
| --- | --- |
| Sil-C | $C_3H_6O(C_2H_4O)_{17}H$ |
| Sil-D | $C_3H_6O(C_2H_4O)_{40}H$ | c. Comparative Nonsilicone Surfactants:

Table 3 provides descriptions of typical, comparative, nonsilicone surfactants, used as agricultural wetting agents.

TABLE 3

Description of Comparative Conventional Nonsilicone Surfactants

| Ref. | Moles EO | Remarks |
| --- | --- | --- |
| OPE | 10 | Octylphenol ethoxylate (TRITON ® X-100) (Union Carbide Corp.) |
| TAE | 15 | Tallow amine ethoxylate (ETHOMEEN ® T/25) (Akzo Nobel) |

Example 2

Surface Tension and Spreading:

This example compares commonly used surfactants with the compositions of the present invention for their ability to provide a reduction of the aqueous surface tension to values below 23 mN/m (Table 4), which is believed to be a requirement for superspreading. The aqueous surface tension was determined by the Wilhelmy plate method, using a sand blasted platinum blade as the sensor. Surfactant solutions (0.1 wt %) were prepared in 0.005 M sodium chloride solution.

Spreading properties: In addition, the compositions of the present invention are demonstrated to provide superspreading properties equivalent to commonly used trisiloxane alkoxylates, Sil-A and Sil-B. Superspreading is defined as a minimum spread diameter of 25 mm on polyester film at ambient conditions. Spreading was determined by applying a 10 μL droplet of surfactant solution to a polyester film (3M, Write-On film) and measuring the spread diameter after 30 seconds. The solution was applied with an automatic pipette to provide droplets of reproducible volume. Deionized water that was further purified with a Millipore filtration system was used to prepare the surfactant solutions.

TABLE 4

Comparison of Surface Tension and Spreading Properties

| Surfactant | Composition of Invention | Surface[a] Tension | Spread Diameter (mm) | |
| --- | --- | --- | --- | --- |
| | | | 0.1 wt % | 0.2 wt % |
| CATSIL-1 | Yes | 20 | 41 | 47 |
| CATSIL-2 | Yes | 20 | 42 | 50 |
| CATSIL-3 | Yes | 20 | 35 | 39 |
| Sil-A | No | 21 | 47 | 42 |
| Sil-B | No | 21 | 48 | 43 |
| Sil-C | No | 25 | 6 | 7 |
| Sil-D | No | 35 | 6 | 7 |
| OPE | No | 29 | 8 | 8 |
| TAE | No | 41 | 7 | 6 |
| None[b] | N/A | 72 | 4 | 4 |

[a]Surface tension in mN/m at 25° C.

TABLE 4-continued

Comparison of Surface Tension and Spreading Properties

| Surfactant | Composition of Invention | Surface[b] Tension | Spread Diameter (mm) 0.1 wt % | 0.2 wt % |
|---|---|---|---|---|

[b]Surface tension of water from CRC Handbook of Chemistry and Physics; 63 Edition, 1982–1983.

Example 3

Herbicide uptake through the waxy cuticle of plants is relatively slow, requiring several hours to achieve maximum penetration. Another mode of entry for agrichemicals is through the stomata found on many plant surfaces. However, only a few specialized surfactants are capable of promoting stomatal infiltration. This mode of entry is rapid (within a few minutes), and chemicals taken up into plants in this way are considered rainfast, meaning that the desired chemical is resistant to wash-off by subsequent rain.

Herbicide uptake at 10 minutes (stomatal infiltration), and 24 hours (stomatal and cuticular penetration) after application was determined by applying solutions of [$^{14}$C] glyphosate, isopropylamine salt (IPAS) to wheat (*Triticum aestivum*) according to the method outlined by Gaskin and Stevens (*Pestic. Sci.* 1993, 38, 185–192). Treatments were applied with and without a surfactant to provide a reference point for uptake enhancement. Uptake measurements were taken at two times: 10 minutes after application to determine stomatal infiltration and 24 hours after application to determine total absorption, including cuticular penetration.

In addition to superspreading ability, organoamine modified trisiloxane alkoxylates provide enhanced uptake of glyphosate into grass (wheat) relative to conventional trisiloxane ethoxylates, which have been shown to antagonize herbicide uptake. Measurements of herbicide uptake at 24 hours after application demonstrate the ability of a surfactant to enhance cuticular penetration. Note that the comparative Sil-A antagonizes glyphosate uptake (Table 5). On the other hand, the compositions of the present invention, CATSIL-2 and CATSIL-3, overcame any antagonism (Table 5; 24 hours after treatment), and provide an enhancement in uptake by comparison to glyphosate alone.

Measurements made at 10 minutes after application demonstrate the ability of a surfactant to promote stomatal infiltration of agrichemicals. Note that the compositions of the present invention (CATSIL-2 and CATSIL-3) as well as the conventional trisiloxane alkoxylate Sil-A all show a modest enhancement in glyphosate uptake by stomatal infiltration, relative to glyphosate alone. The conventional surfactant, TAE, did not enhance the glyphosate uptake within this short time frame, indicating that the TAE is not capable of promoting the infiltration of the stomata of wheat.

TABLE 5

Effect of Surfactant on the Uptake of [$^{14}$C] Glyphosate-IPAS (10 g/L) Into Wheat at 10 Minutes and 24 Hours After Treatment

| Surfactant | Composition of Invention | Wt % Surfactant | Uptake[a] 10 Min. | 24 Hrs |
|---|---|---|---|---|
| None | No | 0 | 3 | 42 |
| CATSIL-2 | Yes | 0.2 | 17 | 79 |
| CATSIL-2 | Yes | 0.5 | 15 | 87 |
| CATSIL-3 | Yes | 0.2 | 18 | 81 |
| CATSIL-3 | Yes | 0.5 | 15 | 83 |
| Sil-A | No | 0.2 | 10 | 26 |
| Sil-A | No | 0.5 | 32 | 46 |
| TAE | No | 0.2 | 3 | 88 |
| TAE | No | 0.5 | 3 | 93 |

[a]LSD (P = 0.05) ± 5.6

Example 4

The effect of adjuvant on glyphosate efficacy was determined using a barley regrowth assay. Glyphosate treatments, with and without adjuvant, were sprayed on barley (14–16 cm tall) at rates of 0.03125, 0.0625, 0.125, 0.25 and 0.5 lbs ae/acre. Six hours after application, all plants were trimmed to 2 cm in height, removing 95% of the treated area. Regrowth was assessed 1 week after treatment by measuring fresh weight and plant height. The data are reported as percent inhibition as compared to the untreated control.

Table 6 is a summary of the data combined across all glyphosate treatments at 0.125 and 0.25%. The compositions of the present invention (CATSIL-1 and CATSIL-2) provided a significant enhancement to glyphosate response (In some cases a 4 fold increase over glyphosate alone). The comparative Sil-A provided no enhancement of glyphosate when used at 0.25%, and only a marginal enhancement at 0.125% as shown in Table 6. One possible explanation for the lower efficacy for treatments with 0.25% surfactant relative to 0.125% as noted in Table 6 is that at 0.25% excessive run off is possible because of the high potential for superspreading.

TABLE 6

Summary of Surfactant Effects, on Glyphosate Activity (Data Pooled Across All Glyphosate Rates)

| Gly/Surfactant Spray Mixture | Wt % Surfactant | % Inhibition Height | % Inhibition (Fresh Wt) |
|---|---|---|---|
| Gly (No Surfactant) | 0 | 11.7e | 9.2 e |
| Gly + Sil-A | 0.125 | 24.5d | 19.4 d |
| Gly + CATSIL-1 | 0.125 | 42.2b | 37.1ab |
| Gly + CATSIL-2 | 0.125 | 47.8a | 43.0 a |
| Gly + Sil-A | 0.25 | 13.4e | 8.6 e |
| Gly + CATSIL-1 | 0.25 | 31.3c | 24.7cd |
| Gly + CATSIL-2 | 0.25 | 39.9b | 36.4 b |
| LSD (0.05) | | 4.9 | 6.4 |

Within columns, different letter means a statistically different result. Data with with no common letters are not statistically different at P<0.05.

Example 5

This example demonstrates that the organoamine modified trisiloxane alkoxylates of the present invention augment glyphosate uptake into gorse, as compared to herbicide alone (Table 7). Although the compositions of the present invention can be cationic, these materials perform similarly to the traditional nonionic trisiloxane alkoxylates as indicated by the lack of statistically significant differences between uptakes by the different siloxanes. This demonstrates that enhanced chemical uptake can be achieved in both grasses as well as other weed species, with the organoamine modified siloxanes of this invention. This is a distinct advantage of these siloxanes, since the prior trisiloxane alkoxylate chemistry antagonizes herbicide performance on grasses, (Example 3 and 4).

TABLE 7

Effect of Surfactant on the Uptake of [$^{14}$C] Glyphosate-IPAS
(10 g/L) into Gorse at 10 Minutes and 24 Hours After Treatment

| Surfactant | Composition of Invention | Wt % Surfactant | Uptake 10 Min.(a) | 24 Hrs(b) |
|---|---|---|---|---|
| None | No | 0 | — | 6 |
| CATSIL-2 | Yes | 0.2 | 23 | 32 |
| Sil-A | No | 0.2 | 36 | 43 |
| CATSIL-2 | Yes | 0.5 | 38 | 55 |
| Sil-A | No | 0.5 | 54 | 57 |

(a)LSD (P = 0.05) = uptake ± 1.26
(b)LSD (P = 0.05) = 15.7

Example 6

The organoamine modified trisiloxane alkoxylate compositions may be used in conjunction with conventional trisiloxane alkoxylates. Table 8 demonstrates that 1:1 blends of the said surfactants provide an increase in stomatal infiltration relative to the organoamine modified trisiloxanes.

TABLE 8

Effect of Surfactant on the Uptake of [$^{14}$C] Glyphosate-IPAS
(10 g/L) Into Bean at 10 Minutes After Treatment

| Surfactant | Composition of Invention | Uptake 10 Min. 0.2% | 0.5% |
|---|---|---|---|
| None | No | --- (2) --- | |
| CATSIL-1 +Sil-B | Yes No | 23 36 | 32 43 |
| CATSIL-2 +Sil-B | Yes No | 38 54 | 55 57 |

I claim:
1. A composition comprising:
   (a) a modified siloxane of the following formula:

   AMe$_2$SiO[(Me)$_2$SiO]$_x$[MeSi(Z)O]$_y$SiMe$_2$A wherein x=0 to 1, y=0 to 2, with the proviso that when y=0, A is Z, A=Me or Z, Z=RO(R$^1$)$_n$R$^2$N(R$^3$)$_2$, R is a divalent organic group of 2 to 4 carbon atoms, R$^1$ is an alkyleneoxide group containing 2 to 4 carbon atoms, R$^2$ is a divalent organic group containing 2 to 6 carbon atoms, R$^3$ is hydrogen, an alkyl radical with 1 to 4 carbons, an amino alkyl of one to four carbons, or an alkyl of 2 to 4 carbon atoms which may have one or more hydroxy substituents thereon, with each R$^3$ being the same or different, and n=1 to 10 if R$^1$ is polyoxyethylene, or n=1 to 5 when R$^1$ is polyoxypropylene, or n=2 to 10 if R$^1$ is a mixture of polyoxyethylene and polyoxypropylene, provided that the ratio of polyoxyethylene to polyoxypropylene is from 0.11 to 9, and n=2 to 10 if at least one R$^1$ is oxybutylene; and
   (b) an acid functional component:
   wherein the composition is superspreading.
2. A composition of claim 1 wherein the acid functionalized component is an acid functional pesticide.

3. A composition according to claim 2 additionally comprising a nonionic surfactant selected from the group consisting of alkyl alkoxylates corresponding to the formula R$^A$—O(R$^C$)$_c$R$^E$ wherein R$^A$ and R$^E$ each denote hydrogen or C$_1$ to C$_{12}$ alkyl (straight or branched chain), R$^C$ denotes alkoxy groups containing 2 or 3 carbon atoms each, and the subscript c is selected so that the molecular weight of the surfactant is 500 to 15,000; and alkoxylated diamines of the formula (H(R$^T$)$_T$)$_2$NC$_2$H$_4$N((R$^T$)$_T$H)$_2$ wherein R$^T$ denotes alkoxy groups containing 2 or 3 carbon atoms each, and the subscript T is selected so that the molecular weight of the alkoxylated diamine is 1,000 to 15,000.
4. A composition of claim 2 where the siloxane is present at a concentration to deliver between 0.01% and 5.0% by weight.
5. A composition according to claim 4 where the acid functional pesticide is selected from the group consisting of: growth regulators, photosynthesis inhibitors, pigment inhibitors, mitotic disrupters, lipid biosynthesis inhibitors, cell wall inhibitors, and cell membrane disrupters.
6. A composition according to claim 5 additionally comprising a nonionic surfactant selected from the group consisting of alkyl alkoxylates corresponding to the formula R$^A$—O(R$^C$)$_c$R$^E$ wherein R$^A$ and R$^E$ each denote hydrogen or C$_1$ to C$_{12}$ alkyl (straight or branched chain), R$^C$ denotes alkoxy groups containing 2 or 3 carbon atoms each, and the subscript c is selected so that the molecular weight of the surfactant is 500 to 15,000; and alkoxylated diamines of the formula (H(R$^T$)$_T$)$_2$NC$_2$H$_4$N((R$^T$)$_T$H)$_2$ wherein R$^T$ denotes alkoxy groups containing 2 or 3 carbon atoms each, and the subscript T is selected so that the molecular weight of the alkoxylated diamine is 1,000 to 15,000.
7. A composition according to claim 4 wherein the acid functional pesticide is a herbicide selected from the group consisting of: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, glufosinate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.
8. A composition according to claim 7 additionally comprising a nonionic surfactant selected from the group consisting of alkyl alkoxylates corresponding to the formula R$^A$—O(R$^C$)$_c$R$^E$ wherein R$^A$ and R$^E$ each denote hydrogen or C$_1$ to C$_{12}$ alkyl (straight or branched chain), R$^C$ denotes alkoxy groups containing 2 or 3 carbon atoms each, and the subscript c is selected so that the molecular weight of the surfactant is 500 to 15,000 [and preferably 1,000 to 8,000]; and alkoxylated diamines of the formula (H(R$^T$)$_T$)$_2$NC$_2$H$_4$N ((R$^T$)$_T$H)$_2$ wherein R$^T$ denotes alkoxy groups containing 2 or 3 carbon atoms each, and the subscript T is selected so that the molecular weight of the alkoxylated diamine is 1,000 to 15,000.
9. A composition according to claim 1 additionally comprising a nonionic siloxane of the formula: R$^5$Me$_2$SiO [Me$_2$SiO]$_f$[MeSi(Q)O]$_g$SiMe$_2$R$^5$ wherein f=0 to 1, g=1 to 2, Q=C$_d$H$_{2d}$O(C$_2$H$_4$O)$_t$(C$_3$H$_6$O)$_w$R$^4$, d=2 to 4, t=3 to 12, w=0 to 8, R$^4$ is hydrogen, acetyl or a hydrocarbon radical between 1 and 4 carbon atoms, and R$^5$ is Q, an alkyl of one to four carbons or a hydroxyl group.
10. A composition according to claim 9 wherein the weight ratio of the nonionic siloxane to the modified siloxane is between 5:95 and 60:40.

11. A composition according to claim 9 wherein $R^1$ is oxyethylene.

12. A composition according to claim 1 wherein x=0 and y=1.

13. A composition according to claim 12 wherein R is propylene, $R^1$ is oxyethylene, $R^2$ is ethylene or propylene, n=2 to 4 and $R^3$ is 2-hydroxyethyl, 2-hydroxypropyl, 3-hydroxypropyl, propyl, or ethyl.

14. A composition according to claim 1 wherein the siloxane is in quaternary ammonium form.

15. A composition according to claim 1 additionally comprising a nonionic surfactant selected from the group consisting of alkyl alkoxylates corresponding to the formula $R^A—O(R^C)_cR^E$ wherein $R^A$ and $R^E$ each denote hydrogen or $C_1$ to $C_{12}$ alkyl (straight or branched chain), $R^C$ denotes alkoxy groups containing 2 or 3 carbon atoms each, and the subscript c is selected so that the molecular weight of the surfactant is 500 to 15,000; and alkoxylated diamines of the formula $(H(R^T)_T)_2NC_2H_4N((R^T)_TH)_2$ wherein $R^T$ denotes alkoxy groups containing 2 or 3 carbon atoms each, and the subscript T is selected so that the molecular weight of the alkoxylated diamine is 1,000 to 15,000.

16. A process for treating plants comprising applying to plants a superspreading composition comprising (a) an effective amount of a modified siloxane of the formula:

$$AMe_2SiO[(Me)_2SiO]_x[MeSi(Z)O]_ySiMe_2A$$

wherein x=0 to 1, y=0 to 2, with the proviso that when y=0, A is Z, A=Me or Z, $Z=RO(R^1)_nR^2N(R^3)_2$, R is a divalent organic group of 2 to 4 carbon atoms, $R^1$ is an alkyleneoxide group containing 2 to 4 carbon atoms, $R^2$ is a divalent organic group containing 2 to 6 carbon atoms, $R^3$ is hydrogen, an alkyl radical with 1 to 4 carbons, an amino alkyl of one to four carbons, or an alkyl of 2 to 4 carbon atoms which may have hydroxy substitutions thereon, with each $R^3$ being the same or different, and n=1 to 10 if $R^1$ is polyoxyethylene, n=1 to 5 when $R^1$ is polyoxypropylene, n=2 to 10 if $R^1$ is a mixture of polyoxyethylene and polyoxypropylene n is from 2 to 10, providing that the ratio of polyoxyethylene and polyoxypropylene is from 0.11 to 9 and when $R^1$ is oxybutylene, there must be sufficient oxyethylene groups such that the resulting siloxane is water dispersible or soluble; and (b) an acid functional pesticide.

17. A process according to claim 16 comprising applying to said plant a composition comprising said modified siloxane an acid functional pesticide and a nonionic siloxane of the formula: $R^5Me_2SiO[Me_2SiO]_f[MeSi(Q)O]_gSiMe_2R^5$ wherein f=0 to 1, g=1 to 2, $Q=C_dH_{2d}O(C_2H_4O)_t(C_3H_6O)_wR^4$, d=2 to 4, 3, t=3 to 12, w=0 to 8, $R^4$ is hydrogen, acetyl or a hydrocarbon radical between 1 and 4 carbon atoms and $R^5$ is Q, or an alkyl of one to four carbons.

18. A process according to claim 17 wherein the weight ratio of the nonionic siloxane to the modified siloxane is between 5:95 and 60:40.

19. A process according to claim 17 wherein $R^1$ is oxyethylene.

20. A process according to claim 16 wherein x=0 and y=1.

21. A process according to claim 16 comprising applying to said plant a composition comprising said modified siloxane, an acid functional pesticide and a nonionic surfactant selected from the group consisting of alkyl alkoxylates corresponding to the formula $R^A—O(R^C)_cR^E$ wherein $R^A$ and $R^E$ each denote hydrogen or $C_1$ to $C_{12}$ alkyl (straight or branched chain), $R^C$ denotes alkoxy groups containing 2 or 3 carbon atoms each, and the subscript c is selected so that the molecular weight of the surfactant is 500 to 15,000 [and preferably 1,000 to 8,000]; and alkoxylated diamines of the formula $(H(R^T)_T)_2NC_2H_4N((R^T)_TH)_2$ wherein $R^T$ denotes alkoxy groups containing 2 or 3 carbon atoms each, and the subscript T is selected so that the molecular weight of the alkoxylated diamine is 1,000 to 15,000.

22. A process according to claim 16 comprising applying to said plant a composition comprising said modified siloxane, an acid functional pesticide, and a nonionic surfactant selected from the group consisting of alkyl alkoxylates corresponding to the formula $R^A—O(R^C)_cR^E$ wherein $R^A$ and $R^E$ each denote hydrogen or $C_1$ to $C_{12}$ alkyl (straight or branched chain), $R^C$ denotes alkoxy groups containing 2 or 3 carbon atoms each, and the subscript c is selected so that the molecular weight of the surfactant is 1,000 to 8,000; and alkoxylated diamines of the formula $(H(R^T)_T)_2NC_2H_4N((R^T)_TH)_2$ wherein $R^T$ denotes alkoxy groups containing 2 or 3 carbon atoms each, and the subscript T is selected so that the molecular weight of the alkoxylated diamine is 1,000 to 15,000.

* * * * *